US012558524B2

(12) United States Patent
Konopacz et al.

(10) Patent No.: US 12,558,524 B2
(45) Date of Patent: Feb. 24, 2026

(54) PREOPERATIVE SKIN PREPARATION APPLICATOR

(71) Applicant: Sage Products, LLC, Cary, IL (US)

(72) Inventors: Kaitlin Konopacz, Cary, IL (US); Alex Chelminski, Cary, IL (US); Claire McCauley, Chicago, IL (US)

(73) Assignee: Sage Products, LLC, Cary, IL (US)

( * ) Notice: Subject to any disclaimer, the term of this patent is extended or adjusted under 35 U.S.C. 154(b) by 395 days.

(21) Appl. No.: 18/122,882

(22) Filed: Mar. 17, 2023

(65) Prior Publication Data

US 2023/0293867 A1 Sep. 21, 2023

Related U.S. Application Data

(60) Provisional application No. 63/414,733, filed on Oct. 10, 2022, provisional application No. 63/321,298, filed on Mar. 18, 2022.

(51) Int. Cl.
*A61M 35/00* (2006.01)
(52) U.S. Cl.
CPC ....... *A61M 35/006* (2013.01); *A61M 2205/19* (2013.01); *A61M 2210/04* (2013.01)
(58) Field of Classification Search
CPC ............ A61M 35/006; A61M 2205/19; A61M 2210/04
See application file for complete search history.

(56) References Cited

U.S. PATENT DOCUMENTS

| | | | |
|---|---|---|---|
| 3,394,702 | A | 7/1968 | Heimlich et al. |
| 3,687,140 | A | 8/1972 | Reynolds |
| 3,774,609 | A | 11/1973 | Schwartzman |
| 3,847,151 | A | 11/1974 | D'Alessandro et al. |
| 3,876,314 | A | 4/1975 | Nehring |
| 3,891,331 | A | 6/1975 | Avery |
| 3,981,304 | A | 9/1976 | Szpur |
| 4,084,910 | A | 4/1978 | Larosa |
| 4,140,409 | A | 2/1979 | DeVries |
| 4,148,318 | A | 4/1979 | Meyer |
| 4,173,978 | A | 11/1979 | Brown |
| 4,225,254 | A | 9/1980 | Holberg et al. |
| 4,291,697 | A | 9/1981 | Georgevich |
| D272,091 | S | 1/1984 | Kaufman |
| 4,430,013 | A | 2/1984 | Kaufman |
| 4,432,749 | A | 2/1984 | Snyder et al. |

(Continued)

*Primary Examiner* — Jessica Arble
(74) *Attorney, Agent, or Firm* — FOLEY & LARDNER LLP

(57) ABSTRACT

An applicator device configured for delivery of at least one solution to a surface, includes an applicator body having a head portion including an opening, a distal end, and an outer wall forming an interior space, and a fluid container moveably positioned in the interior space of the applicator body, the fluid container having an interior portion for holding the at least one solution and a membrane for preventing passage of the solution out of the interior portion. The device further includes a piercing element configured to breach the membrane to allow for passage of the solution out of the interior space of the fluid container, and a distal cap coupled to the distal end of the applicator body configured such that rotation of the distal cap causes longitudinal movement of the fluid container within the interior space of the applicator body into contact with the piercing element.

20 Claims, 12 Drawing Sheets

(56) References Cited

U.S. PATENT DOCUMENTS

| | | | |
|---|---|---|---|
| D274,098 S | 5/1984 | Kaufman | |
| D274,160 S | 6/1984 | Kaufman | |
| 4,507,111 A | 3/1985 | Gordon et al. | |
| 4,519,795 A | 5/1985 | Hitchcock et al. | |
| 4,701,168 A | 10/1987 | Gammons | |
| 4,784,506 A | 11/1988 | Koreska et al. | |
| 4,799,815 A | 1/1989 | Barabino et al. | |
| 4,886,388 A | 12/1989 | Gulker et al. | |
| 4,887,994 A | 12/1989 | Bedford | |
| 4,925,327 A | 5/1990 | Wirt | |
| 4,957,385 A | 9/1990 | Weinstein | |
| 5,006,004 A | 4/1991 | Dirksing et al. | |
| 5,120,301 A | 6/1992 | Wu | |
| 5,308,180 A | 5/1994 | Pournoor et al. | |
| D351,229 S | 10/1994 | Wirt | |
| 5,445,462 A | 8/1995 | Johnson et al. | |
| 5,489,280 A | 2/1996 | Russell | |
| 5,509,744 A | 4/1996 | Frazier | |
| 5,538,353 A | 7/1996 | Dehavilland | |
| D375,354 S | 11/1996 | Haber et al. | |
| 5,597,255 A | 1/1997 | Yager et al. | |
| D379,507 S | 5/1997 | Haber et al. | |
| 5,658,084 A | 8/1997 | Wirt | |
| 5,690,958 A | 11/1997 | McGrath | |
| 5,713,843 A | 2/1998 | Vangsness | |
| 5,772,346 A | 6/1998 | Edwards | |
| 5,779,053 A | 7/1998 | Partika et al. | |
| 5,791,801 A | 8/1998 | Miller | |
| D404,125 S | 1/1999 | Weinstein | |
| 5,908,256 A | 6/1999 | Bernstein | |
| 5,915,746 A | 6/1999 | Melcher et al. | |
| D416,389 S | 11/1999 | Frazier | |
| D421,302 S | 2/2000 | Korteweg | |
| 6,190,367 B1 | 2/2001 | Hall | |
| 6,245,037 B1 | 6/2001 | Reum et al. | |
| 6,248,085 B1 | 6/2001 | Scholz et al. | |
| 6,299,377 B1 | 10/2001 | Emerit et al. | |
| 6,371,675 B1 | 4/2002 | Hoang et al. | |
| D458,367 S | 6/2002 | Zaspel et al. | |
| 6,439,789 B1 | 8/2002 | Ballance et al. | |
| 6,488,665 B1 | 12/2002 | Severin et al. | |
| 6,533,484 B1 | 3/2003 | Osei et al. | |
| 6,536,975 B1 | 3/2003 | Tufts | |
| 6,565,840 B1 | 5/2003 | Clark et al. | |
| 6,595,940 B1 | 7/2003 | D'Alessio et al. | |
| 6,695,515 B1 | 2/2004 | Fleury | |
| 6,755,586 B1 | 6/2004 | Frazier | |
| 6,821,043 B2 | 11/2004 | Teh | |
| D503,229 S | 3/2005 | Davis et al. | |
| D506,028 S | 6/2005 | Dickey | |
| 6,910,822 B2 | 6/2005 | Hidle et al. | |
| 6,916,133 B2 | 7/2005 | Hoang et al. | |
| 7,008,132 B1 | 3/2006 | Phua et al. | |
| 7,008,133 B2 | 3/2006 | Ashe et al. | |
| 7,182,536 B2 | 2/2007 | Tufts et al. | |
| 7,201,525 B2 | 4/2007 | Mohiuddin | |
| 7,377,710 B2 | 5/2008 | Baumann et al. | |
| 7,422,388 B2 | 9/2008 | Tufts et al. | |
| 7,441,973 B2 | 10/2008 | Voegele et al. | |
| 7,540,681 B2 | 6/2009 | Cybulski et al. | |
| 7,866,471 B2 | 1/2011 | Callahan et al. | |
| 7,993,066 B2 | 8/2011 | Flores et al. | |
| 8,001,645 B2 | 8/2011 | Kaufman et al. | |
| 8,047,735 B2 | 11/2011 | Broadley et al. | |
| 8,061,917 B2 | 11/2011 | Stenton et al. | |
| 8,118,766 B2 | 2/2012 | Davis et al. | |
| 8,235,617 B2 | 8/2012 | Peck et al. | |
| 8,348,913 B2 | 1/2013 | Hoang et al. | |
| D678,783 S | 3/2013 | Wilcox et al. | |
| D679,003 S | 3/2013 | Jupin | |
| 8,388,248 B2 | 3/2013 | Jemsby et al. | |
| 8,518,076 B2 | 8/2013 | Stenton | |
| 8,550,737 B2 | 10/2013 | Ruiz et al. | |
| 8,556,529 B2 | 10/2013 | Law et al. | |
| 8,740,488 B2 | 6/2014 | Cable et al. | |
| 8,740,831 B2 | 6/2014 | Wu | |
| 8,790,031 B2 | 7/2014 | Mcdonald | |
| 8,790,032 B2 | 7/2014 | Quintero et al. | |
| 8,801,312 B2 | 8/2014 | Guzman et al. | |
| 8,852,231 B2 | 10/2014 | Mach et al. | |
| 8,858,515 B2 | 10/2014 | Cornell | |
| 8,864,399 B2 | 10/2014 | Guzman et al. | |
| 8,911,771 B2 | 12/2014 | Vanek et al. | |
| 8,956,065 B2 | 2/2015 | Froimson et al. | |
| 8,979,785 B2 * | 3/2015 | Korogi | A61M 35/006 |
| | | | 604/289 |
| 8,986,236 B2 | 3/2015 | Slokovic et al. | |
| 9,016,967 B2 | 4/2015 | Law et al. | |
| 9,074,434 B2 | 7/2015 | Mensa-Wilmot | |
| 9,119,946 B2 | 9/2015 | Dokken et al. | |
| 9,150,045 B2 | 10/2015 | Gurtner et al. | |
| 9,265,923 B2 | 2/2016 | Boone et al. | |
| 9,283,364 B2 | 3/2016 | Lockwood et al. | |
| 9,408,521 B2 | 8/2016 | Molinet et al. | |
| D767,121 S | 9/2016 | Dombrowski et al. | |
| 9,481,005 B2 | 11/2016 | Margoosian et al. | |
| D776,266 S | 1/2017 | Dombrowski et al. | |
| D776,267 S | 1/2017 | Dombrowski et al. | |
| D777,909 S | 1/2017 | Dombrowski et al. | |
| D780,307 S | 2/2017 | Mingione et al. | |
| 9,566,421 B2 | 2/2017 | Casey et al. | |
| 9,572,967 B2 | 2/2017 | Mcdonald et al. | |
| 9,597,062 B2 | 3/2017 | Alexander et al. | |
| 9,629,368 B2 | 4/2017 | Ash et al. | |
| D789,521 S | 6/2017 | Dombrowski et al. | |
| 9,675,787 B2 | 6/2017 | Guzman | |
| 9,688,444 B2 | 6/2017 | Kinsman et al. | |
| D791,307 S | 7/2017 | Mingione et al. | |
| 9,724,724 B2 | 8/2017 | Goad et al. | |
| 9,750,922 B2 | 9/2017 | Hoang et al. | |
| 9,757,551 B2 | 9/2017 | Degala et al. | |
| 9,775,977 B2 | 10/2017 | Dombrowski et al. | |
| 9,782,573 B2 | 10/2017 | Margoosian et al. | |
| 9,789,297 B2 | 10/2017 | Dombrowski et al. | |
| D806,238 S | 12/2017 | Hashimoto et al. | |
| D815,734 S | 4/2018 | Burke | |
| 9,943,157 B1 | 4/2018 | Chang | |
| 9,950,554 B2 | 4/2018 | Maiwald et al. | |
| 9,968,764 B2 | 5/2018 | Guzman | |
| 9,980,784 B2 | 5/2018 | Fasolino et al. | |
| 9,987,474 B2 | 6/2018 | Adams et al. | |
| 10,004,843 B2 | 6/2018 | Hamilton et al. | |
| 10,076,465 B2 | 9/2018 | Smith | |
| 10,076,648 B2 | 9/2018 | Mingione et al. | |
| 10,092,737 B2 | 10/2018 | Quaglia | |
| 10,149,735 B2 | 12/2018 | Noell et al. | |
| 10,159,823 B2 | 12/2018 | Tidwell | |
| 10,173,041 B2 | 1/2019 | Law | |
| 10,220,194 B2 | 3/2019 | Battaglia | |
| D848,611 S | 5/2019 | Skakoon | |
| 10,335,582 B2 | 7/2019 | Wolfenbarger | |
| 10,350,937 B2 | 7/2019 | Fehlmann et al. | |
| 10,405,634 B2 | 9/2019 | Kirk et al. | |
| D864,382 S | 10/2019 | Adams et al. | |
| 10,426,939 B2 | 10/2019 | Klaassen | |
| 10,442,598 B2 | 10/2019 | May et al. | |
| 10,471,244 B2 | 11/2019 | Dombrowski et al. | |
| 10,478,167 B2 | 11/2019 | Russo | |
| 10,478,602 B2 | 11/2019 | Adams et al. | |
| 10,549,078 B2 | 2/2020 | Mingione et al. | |
| 10,576,256 B2 | 3/2020 | Souza et al. | |
| 10,610,200 B2 | 4/2020 | Arant et al. | |
| 10,675,909 B2 | 6/2020 | Bezuhly | |
| 10,688,291 B2 | 6/2020 | Durham et al. | |
| 10,689,152 B2 | 6/2020 | May et al. | |
| 10,729,720 B2 | 8/2020 | Shanler et al. | |
| 10,744,309 B1 | 8/2020 | Ware et al. | |
| 10,765,849 B2 | 9/2020 | Chiang et al. | |
| 10,813,892 B2 | 10/2020 | Mcginley et al. | |
| 10,828,477 B2 | 11/2020 | Kaufman et al. | |
| 10,842,899 B1 | 11/2020 | Alfattani | |
| 11,027,032 B2 | 6/2021 | Degala et al. | |
| 2002/0076255 A1 | 6/2002 | Hoang et al. | |
| 2002/0076258 A1 | 6/2002 | Crosby et al. | |

(56)　　　　　References Cited

U.S. PATENT DOCUMENTS

| | | | |
|---|---|---|---|
| 2003/0233063 A1 | 12/2003 | Nakatani | |
| 2004/0086321 A1 | 5/2004 | Burkholz et al. | |
| 2004/0162533 A1 | 8/2004 | Alley | |
| 2004/0240927 A1* | 12/2004 | Hoang | A61M 35/006 |
| | | | 401/133 |
| 2004/0267182 A1* | 12/2004 | Davis | A61M 35/006 |
| | | | 604/2 |
| 2005/0049538 A1 | 3/2005 | Trevillot | |
| 2005/0054967 A1 | 3/2005 | Ashe et al. | |
| 2005/0175786 A1 | 8/2005 | Singh et al. | |
| 2005/0222542 A1 | 10/2005 | Burkholz et al. | |
| 2005/0261639 A1 | 11/2005 | Herweck | |
| 2005/0262811 A1 | 12/2005 | Mohiuddin | |
| 2006/0282035 A1 | 12/2006 | Battisti et al. | |
| 2007/0009317 A1 | 1/2007 | Phua | |
| 2007/0066927 A1 | 3/2007 | Akelman et al. | |
| 2007/0147946 A1* | 6/2007 | Cybulski | A61M 35/003 |
| | | | 401/133 |
| 2007/0282241 A1 | 12/2007 | Squires | |
| 2008/0003052 A1 | 1/2008 | Lee et al. | |
| 2008/0071208 A1 | 3/2008 | Voegele et al. | |
| 2008/0219750 A1 | 9/2008 | Siegel | |
| 2008/0298879 A1 | 12/2008 | Chesak et al. | |

| | | | |
|---|---|---|---|
| 2009/0088705 A1 | 4/2009 | Sirkin | |
| 2010/0114000 A1 | 5/2010 | Park et al. | |
| 2012/0043346 A1 | 2/2012 | Nentwick et al. | |
| 2012/0143153 A1* | 6/2012 | Cable, Jr. | A61M 35/003 |
| | | | 604/310 |
| 2014/0081221 A1 | 3/2014 | Mcdonald et al. | |
| 2014/0081222 A1 | 3/2014 | Mcdonald et al. | |
| 2015/0126944 A1 | 5/2015 | Stemer | |
| 2016/0158505 A1 | 6/2016 | Rauchwerger et al. | |
| 2017/0217244 A1* | 8/2017 | Fehlmann | B05C 17/00 |
| 2017/0348517 A1 | 12/2017 | Colombo | |
| 2018/0043145 A1 | 2/2018 | Hendriks et al. | |
| 2018/0161559 A1 | 6/2018 | Sei et al. | |
| 2018/0161561 A1 | 6/2018 | Shiozaki et al. | |
| 2018/0333566 A1 | 11/2018 | Follman et al. | |
| 2019/0009068 A1 | 1/2019 | Margoosian et al. | |
| 2019/0076634 A1 | 3/2019 | Mchugh | |
| 2019/0170543 A1 | 6/2019 | Rothenberg et al. | |
| 2019/0209816 A1* | 7/2019 | Follman | A61M 35/006 |
| 2019/0269894 A1 | 9/2019 | Yarger et al. | |
| 2019/0339174 A1 | 11/2019 | O'Neill | |
| 2019/0351203 A1 | 11/2019 | Mcguire, Jr. | |
| 2020/0040291 A1 | 2/2020 | Hakimi et al. | |
| 2020/0138169 A1 | 5/2020 | Silber | |
| 2020/0214423 A1 | 7/2020 | Samangooie | |
| 2021/0052825 A1 | 2/2021 | Lynch et al. | |

* cited by examiner

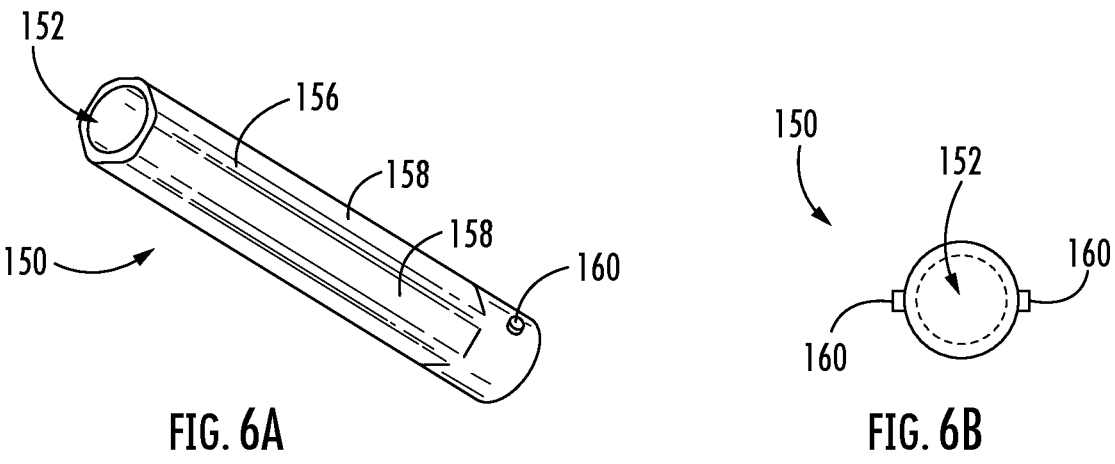
FIG. 6A
FIG. 6B
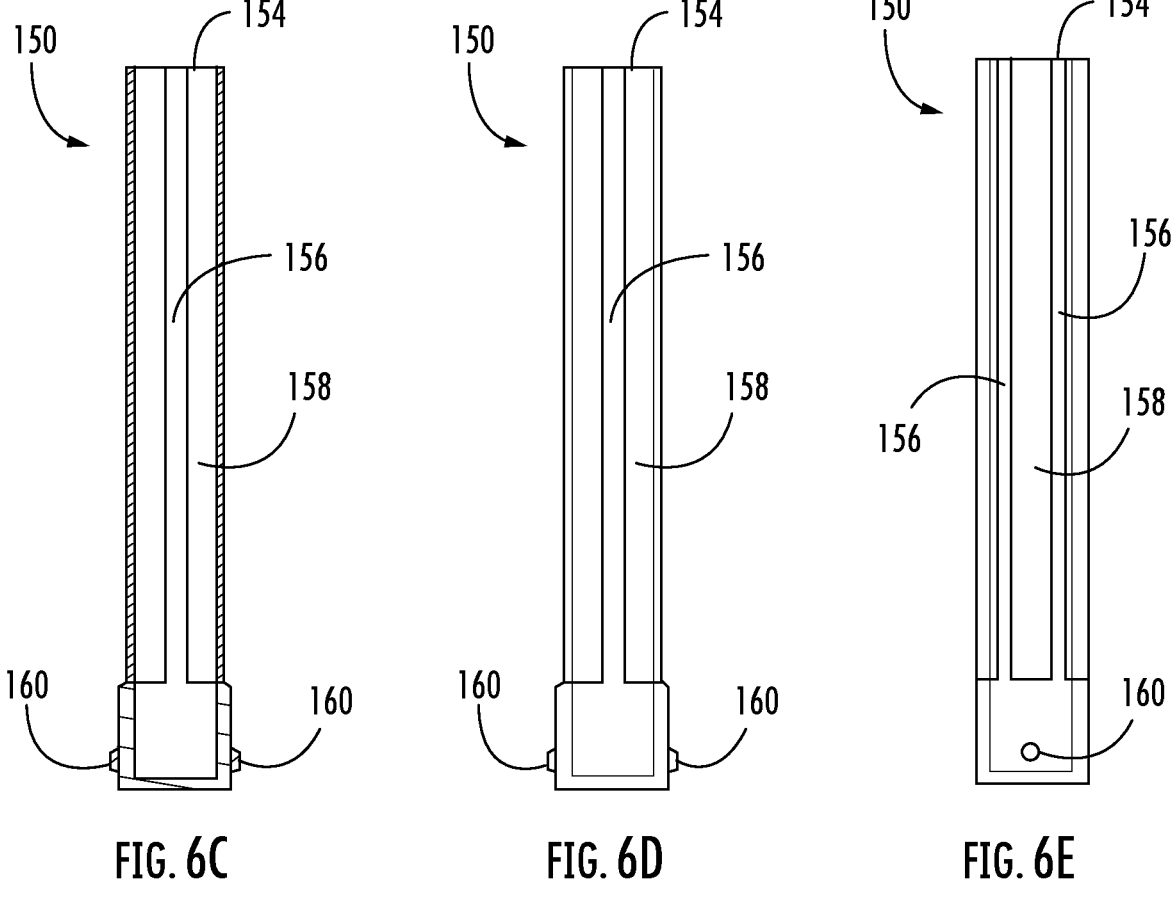
FIG. 6C
FIG. 6D
FIG. 6E

PREOPERATIVE SKIN PREPARATION APPLICATOR

CROSS-REFERENCE TO RELATED APPLICATIONS

This application claims the benefit of and priority to U.S. Provisional Patent Application Ser. No. 63/321,298, filed Mar. 18, 2022 and U.S. Provisional Patent Application Ser. No. 63/414,733, filed Oct. 10, 2022, both of which are hereby incorporated by reference in their entireties.

BACKGROUND

The present disclosure relates generally to the field of preoperative skin preparation. More specifically, the disclosure relates to a device for containing and dispensing solution for use during preoperative skin preparation.

Currently available applicators and dispensers of preoperative skin preparation solutions can become inadvertently activated from accidental and/or excessive pressure during transportation and use due to the mechanism of activation. Additionally, at times, the solution contained within the applicator or container does not fully or properly leave the container when the device is activated.

The present disclosure seeks to overcome certain of these limitations and other drawbacks of existing devices and applicators for delivering a preoperative skin care solution, and to provide new features that are not heretofore available.

BRIEF DESCRIPTION OF THE FIGURES

The disclosure will become more fully understood from the following detailed description, taken in conjunction with the accompanying figures, wherein like reference numerals refer to like elements, in which:

FIG. 6A is a top perspective view of a fluid container, according to an exemplary embodiment.

FIG. 6B is a top view of the fluid container of FIG. 6A.

FIG. 6C is a side cross-section view of the fluid container of FIG. 6A.

FIG. 6D is a side view of the fluid container of FIG. 6A.

FIG. 6E is a front view of the fluid container of FIG. 6A.

DETAILED DESCRIPTION

Before turning to the figures, which illustrate certain exemplary embodiments in detail, it should be understood that the present disclosure is not limited to the details or methodology set forth in the description or illustrated in the figures. It should also be understood that the terminology used herein is for the purpose of description only and should not be regarded as limiting.

Figure 1:
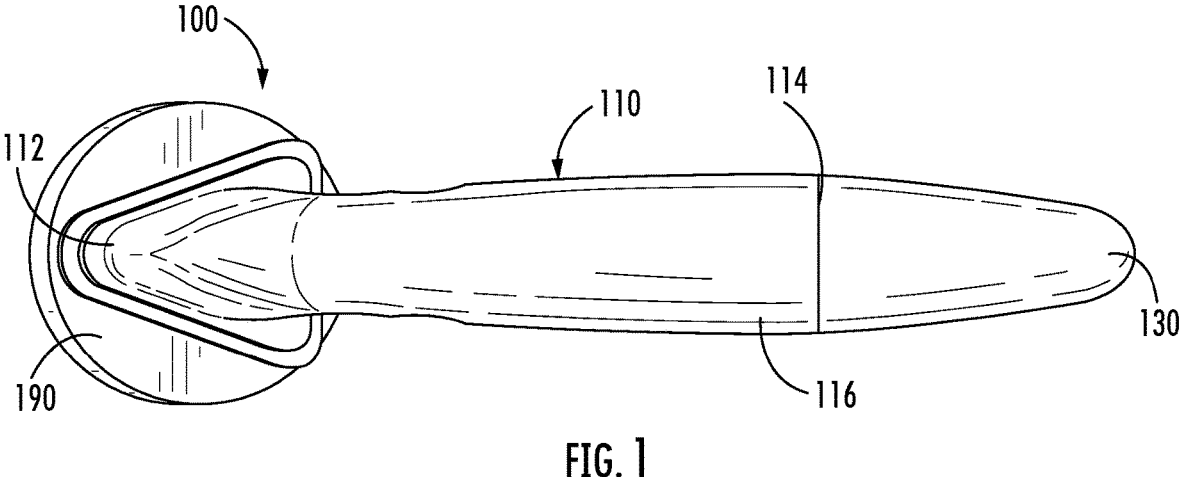
FIG. 1 is top view of an applicator device, according to an exemplary embodiment.
Figure 2:
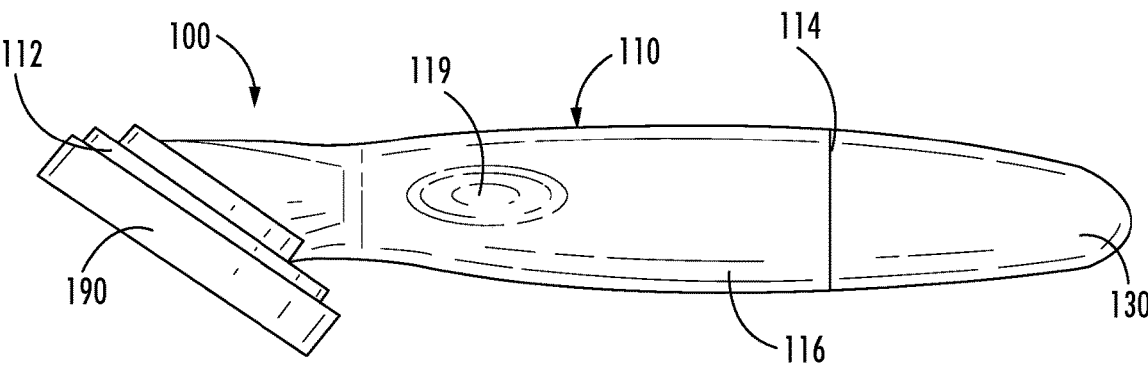
FIG. 2 is side view of the applicator device of FIG. 1.

An applicator device, according to an exemplary embodiment is shown in FIGS. 1-7D. In various implementations, the applicator device 100 is configured for storing and dispensing one or more solutions for preoperative preparation (e.g., disinfecting, cleansing, etc.) of a patient's skin or other anatomy. As shown in FIGS. 1-2, the applicator device 100 includes an applicator body 110 having a head portion 112 (including opening 113), a distal end 114, and an outer wall 116 forming an interior space 118 (not shown in FIG. 1). The distal end 114 of the applicator body 110 is coupled to distal cap 130. The head portion 112 of the applicator body 110 is coupled to an absorbent element 190, such as a sponge or a piece of foam material configured to contact the patient's skin for delivery of a solution thereto. Referring to FIG. 2, the applicator body 110 may include one or more gripping elements, such as indents 119 to aide in gripping of the applicator device 100 by the user (e.g., healthcare provider, medical personnel, caretaker, etc.).

Figure 3:
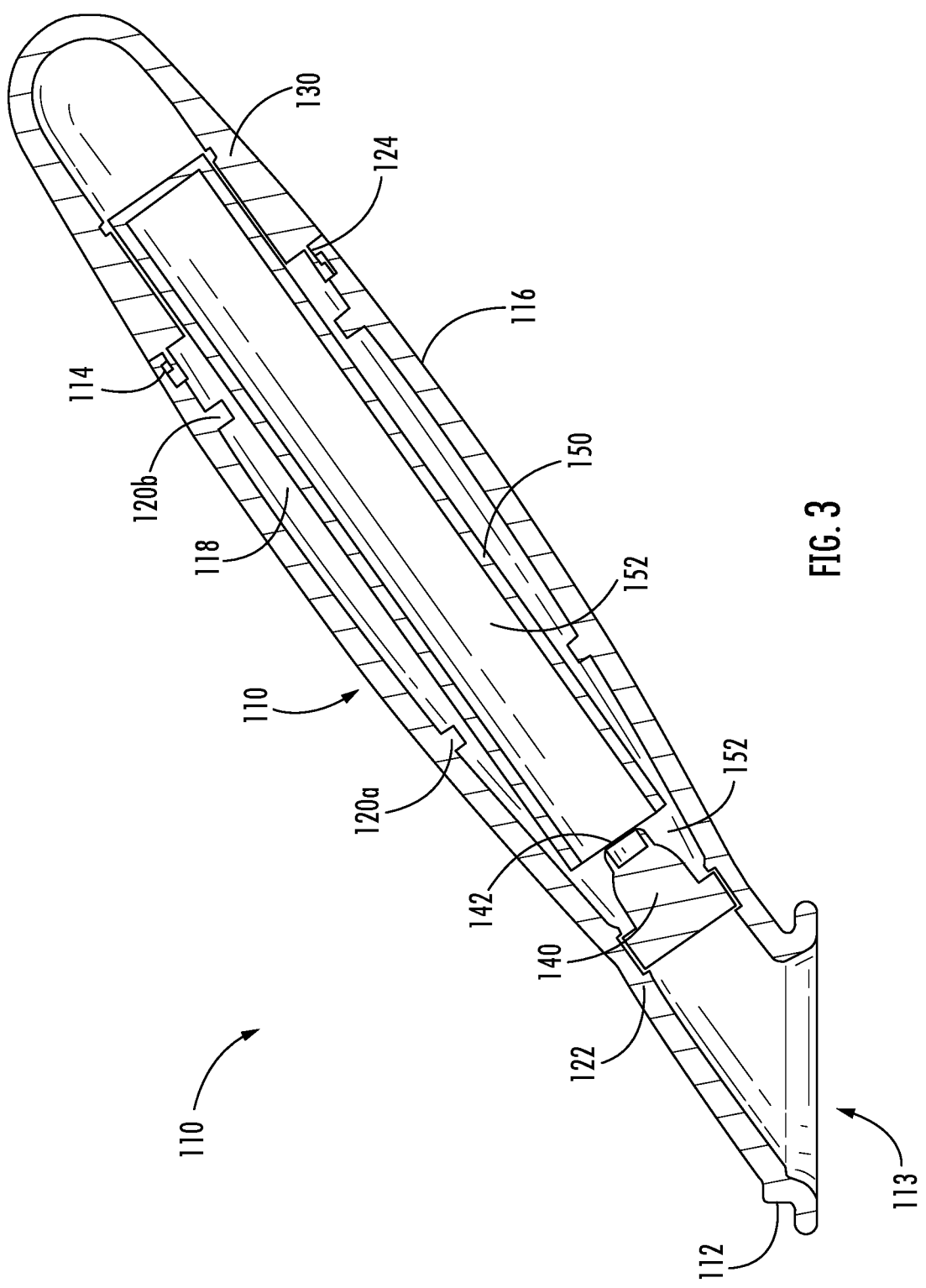
FIG. 3 is cross-sectional side view of the applicator device of FIG. 1.
Figure 4A:
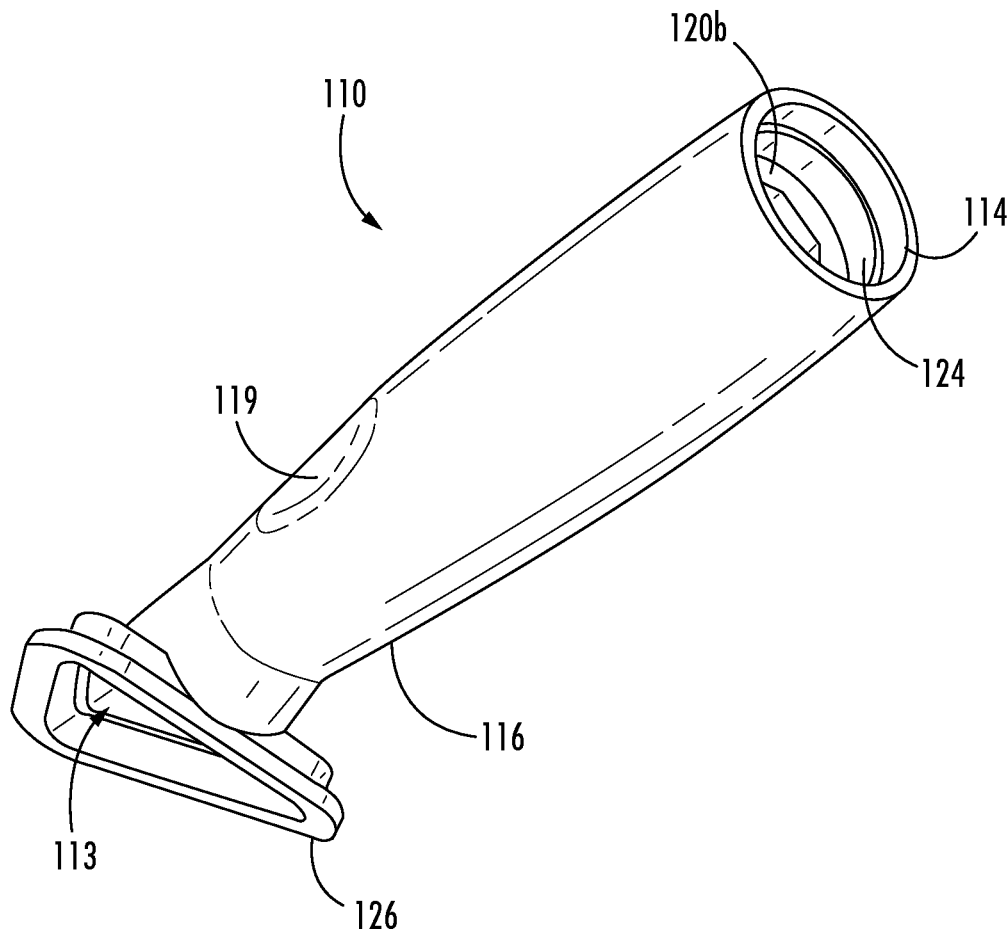
FIG. 4A a bottom perspective view of an applicator body of the applicator device of FIG. 1.
Figures 4B, 4C, 4D:
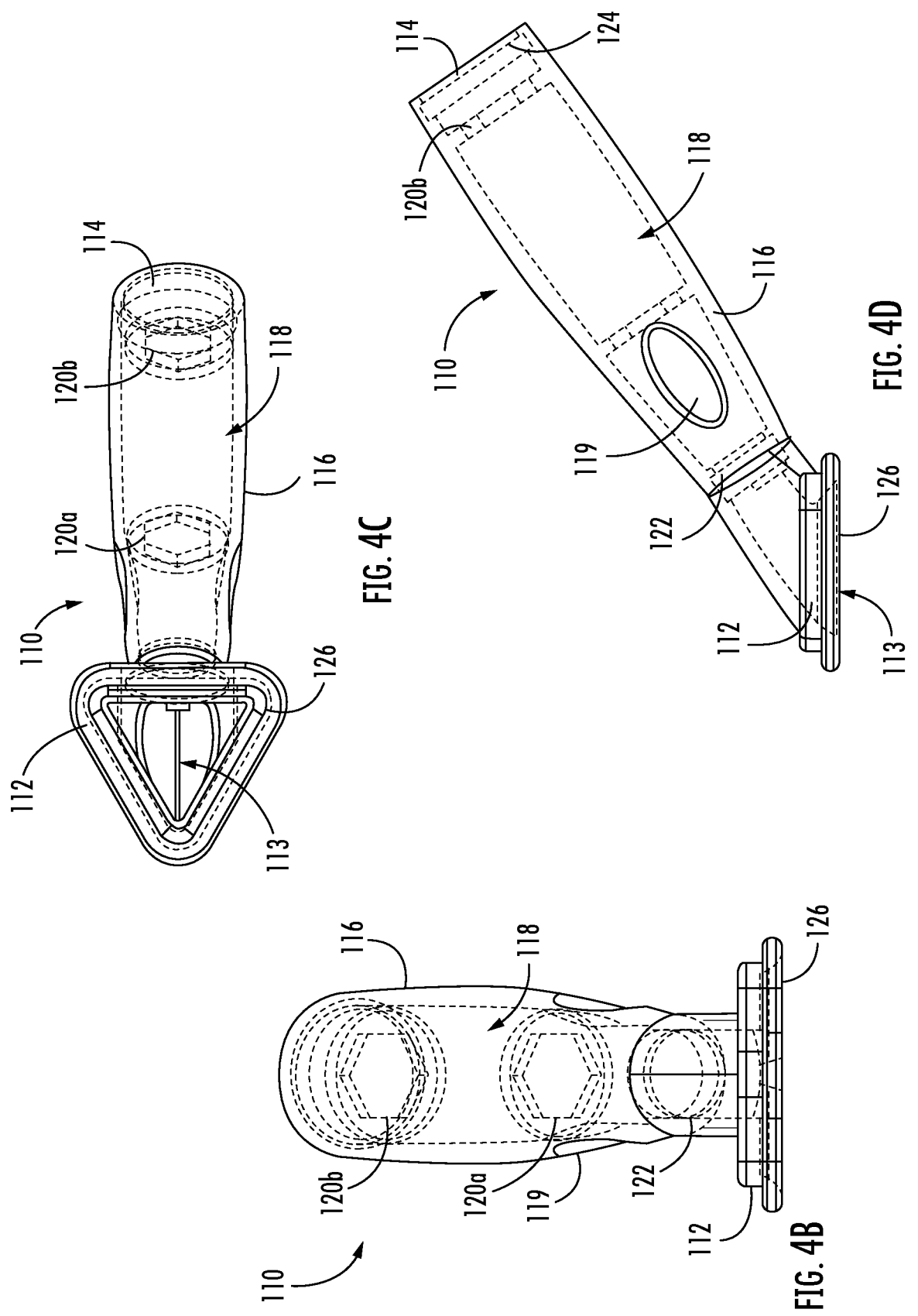
FIG. 4B is a front view of the applicator body of FIG. 4A.
FIG. 4C is a bottom view of the applicator body of FIG. 4A.
FIG. 4D is a side view of the applicator body of FIG. 4A.
Figure 5A:
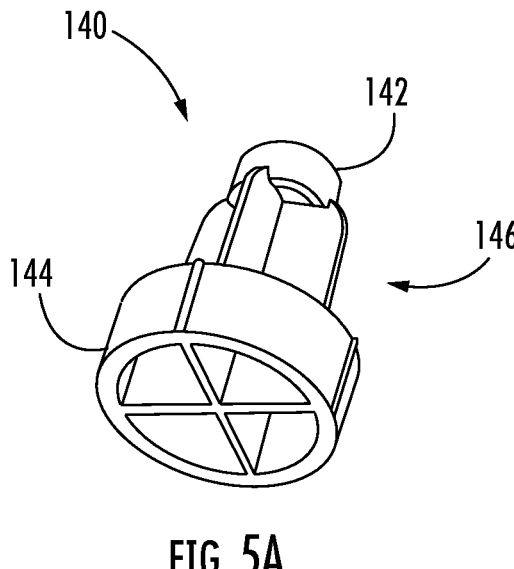
FIG. 5A is a bottom perspective view of a piercing element, according to an exemplary embodiment.
Figure 5B:
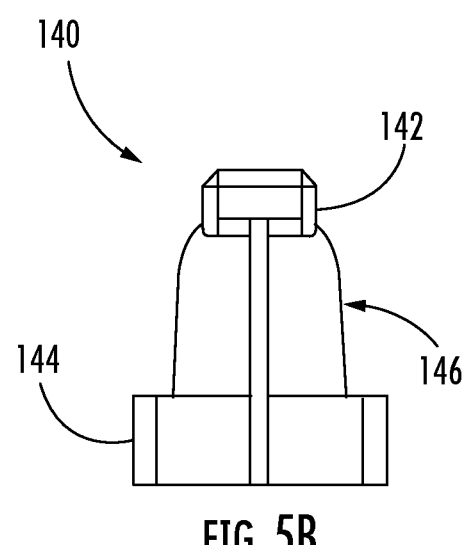
FIG. 5B is a side cross-section view of the piercing element of FIG. 5A.
Figure 5C:
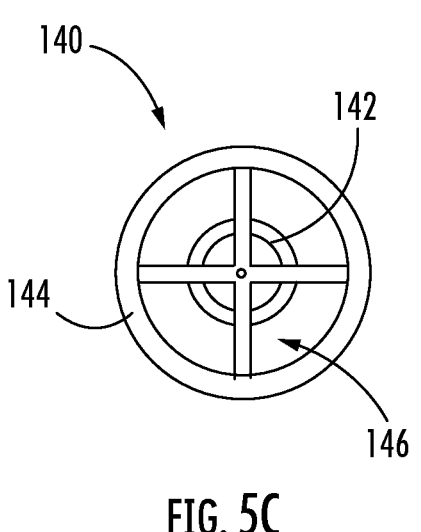
FIG. 5C is a bottom view of the piercing element of FIG. 5A.
Figure 5D:
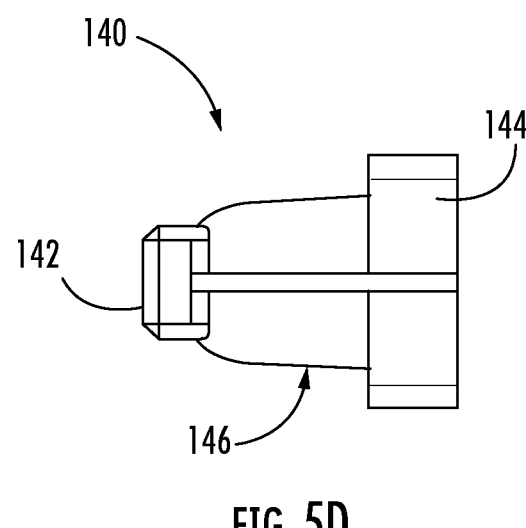
FIG. 5D is a side view of the piercing element of FIG. 5A.
Figures 7A, 7B:
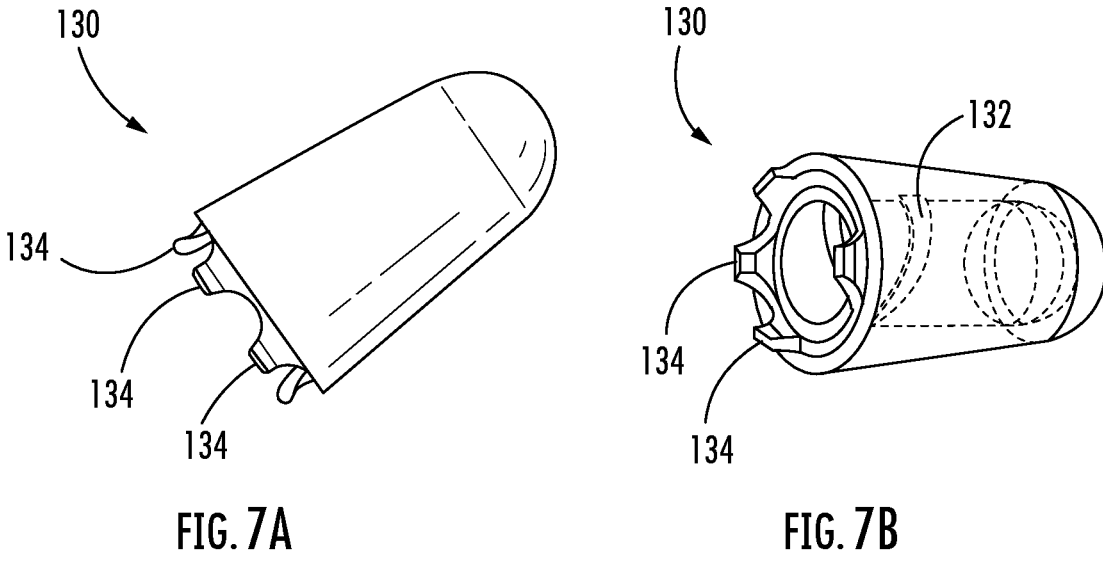
FIG. 7A is a perspective view of a distal cap, according to an exemplary embodiment.
FIG. 7B is a bottom side perspective view of the distal cap of FIG. 7A.
Figures 7C, 7D:
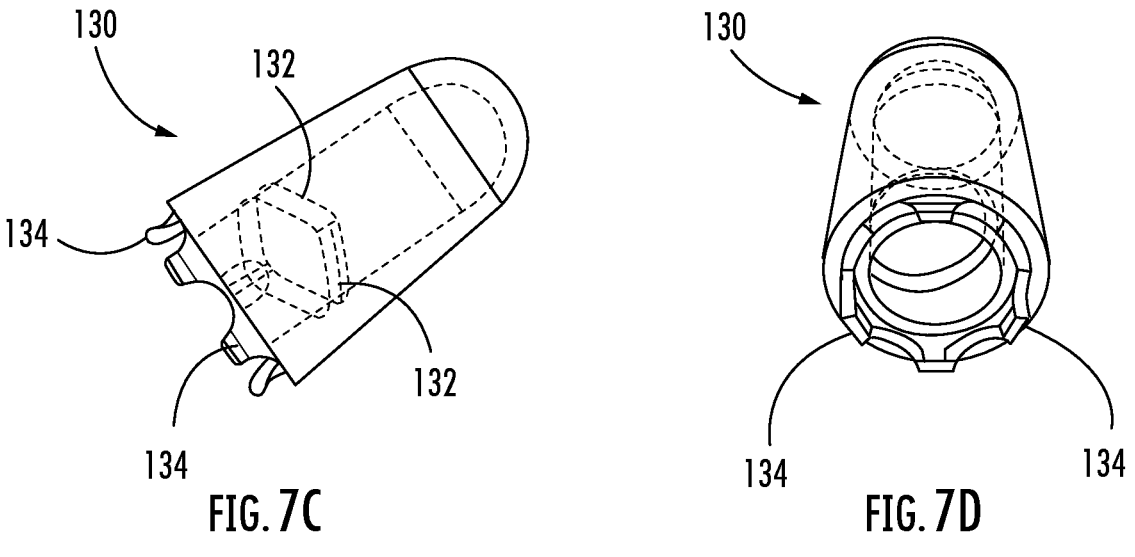
FIG. 7C is a side perspective view of the distal cap of FIG. 7A.
FIG. 7D is bottom front perspective view of the distal cap of FIG. 7A.

FIG. 3 shows a longitudinal cross-section of the applicator device 100 and additional components positioned within the interior space 118, including a fluid container 150 and a piercing element 140. The fluid container 150 includes an interior portion 152 configured to hold the solution therein, and is sealed by a membrane 154 at a proximal end of the interior portion 152 (see FIGS. 6C-6E) which prevents passage of the solution from the fluid container 150 until use (e.g., during transport, storage, etc.). The membrane 154 may be formed from a film such as plastic, foil, or other frangible material allowing for a breakable seal.

The fluid container 150 is moveably positioned within the interior space 118 between a first position and a second position. In the first position, the membrane 154 of the fluid container is separated from a tip 142 of the piercing element 140, or alternatively, is only in touching contact with the tip 142 (as depicted in FIG. 3). In the second position, the membrane 154 is moved beyond the tip 142 of the piercing element such that the tip 142 breaches the membrane 154 and allows for the passage of fluid from the fluid container 150. When the membrane 154 is breached, solution from the fluid container 150 is able to flow through and past the piercing element 140, through the head portion 112 and opening 113, and into the absorbent element 190 (see FIGS. 1-2) for delivery to the patient's skin.

The applicator body 110, according to an exemplary embodiment, is shown in FIGS. 4A-4D. As shown, the interior space 118 of the applicator body includes various features to accommodate the additional components held within the interior space 118, such as the fluid container 150 and the piercing element 140. For example, in the embodiment shown in FIGS. 4A-4D the interior space 118 has areas of differing diameters. For example, the interior space 118 may have contained therein one or more anti-rotation fittings 120*a*, 120*b* which form a hexagon having a decreased diameter relative to the rest of the interior space 118. The hexagon shape is configured to interact with an outer surface configuration of the fluid container 150, as discussed in more detail below, in order to prevent rotation (spinning) of the fluid container 150 within the interior space 118. The interior space also includes a fitting 122 for the piercing elements 140, as well as at least one ridge 124 or other suitable connection element at the distal end for receiving and/or engaging with clips or flanges associated with the distal cap 130, for a snap fit connection therewith. In other embodiments, the distal cap 130 may be threaded on to the applicator body 110. In yet other embodiments, the distal cap 130 may be press fit, friction fit, adhered, or otherwise coupled to the applicator body 110 using any suitable method known in the art.

The head portion 112 of the applicator body 110 engages with the absorbent element 190 at a connection end 126. In the embodiment shown in the figures, the connection end 126 is in the shape of a triangle, however other shapes and configurations, such as a circle, square, oval, hexagon, etc. For example, the connection end 126 and/or absorbent element 190 may have a round shape, rectangular shape, trapezoidal shape, or any other shape that would allow for distribution of the solution to difficult to reach areas and/or smaller areas of the surface of the patient (e.g., between fingers or toes, etc.). In various embodiments, the connection end 126 may have a shape that is complementary to the shape of the absorbent element 190. The opening 113 in the head portion is in fluid communication between the interior space 118 of the applicator body 110 and through the connection end 126.

In some embodiments, the head portion is designed such that the plane of the connection end 126 is disposed at an angle relative to a longitudinal axis of the applicator body 110, for example at an angle between 20 degrees and 45 degrees relative to a longitudinal axis of the applicator body 110. In other embodiments, the plane of the connection end 126 may be substantially perpendicular to the longitudinal axis of the applicator body 110.

The piercing element, according to an exemplary embodiment, is shown in FIGS. 5A-5D. As shown, the piercing element 140 includes a tip 142 and a base portion 144. As shown, the piercing element 140 is not an entirely solid element, but instead takes on a frame 146 arrangement including openings and passageways to facilitate the flow of fluid.

The piercing element 140 is design in such a way as to pierce and/or open up the fluid container 150 wide enough to allow the fluid contained within to drain out quickly and completely. For example, the base and outer frame portions of the piercing element 140 have a diameter that is substantially the same as the inner diameter of the fluid container 150. In some embodiments, the shape of tip portion 142 may be a cross or circle with one or more sharp points intended to create a point force to easily pierce or open the containment vessel. In some embodiments, the tip 142 is somewhat blunt. The tip portion 142 may also not feature any points, but thinner material in order to create the point force.

In addition to the design of the piercing element 140 to assist with efficient and complete draining of the solution, the fluid container 150, described in further detail below, may also feature an angled top or chute on the inside or outside of the fluid container 150 in order to allow the liquid to more quickly drain out. These features work by disrupting the surface tensions of the solution and also providing a way for air to enter into the fluid container 150 in order to overcome the pressure differential when the membrane 154 of the fluid container 150 is breached.

The fluid container 150, according to an exemplary embodiment, is shown in FIGS. 6A-6E. The fluid container 150 includes an interior portion 152 for carrying a fluid, such as the preoperative skin preparation solution, and a membrane 154 positioned at a proximal end of interior portion 152 which prevents passage of the solution from the fluid container 150 until use (e.g., during transport, storage, etc.). The membrane 154 is configured to be breached by the piercing element 150, described above.

According to an exemplary embodiment, the interior portion 152 has a generally circular interior cross-section, though other geometric shapes are possible. In the embodiments shown, the exterior surfaces of the fluid container 150 have a plurality of ridges 156 and flat faces 158, thereby forming a hexagonal cross-section. The hexagonal cross-section, in coordination with the design of the inner bore 120 of the applicator body 110 prevents rotation of the fluid container 150 relative to the applicator body 110, which is important to the twisting activation of the device, discussed below. Though the embodiment shown includes six ridges 156 and six flat faces 158, any number of ridges 156 and flat faces 158 may be used.

According to an exemplary embodiment, the fluid container 150 further includes at least one projection 160 extending radially from the outer surface of the fluid container 150. In some embodiments, the number of projections 160 is two and the projections are directly opposite (see FIGS. 6B-6D) from one another on the outside of the fluid container 150.

The projections 160 are configured to engage with at least one guide channel, such as helical slot 132, in the distal cap 130, shown in FIGS. 7A-7D according to an exemplary embodiment. The number of helical slots 132 correspond with the number of projections 160 present on the fluid container 150. In the embodiment shown, there are two helical slots 132. The helical slots 132 are formed in the inner surface of the distal cap 130. In this way, the projections 160 are driven once the distal cap 140 is twisted. Specifically, the at least one projection 160 and at least one slot 132 will convert rotational energy into translational energy which will drive the fluid container 150 longitudinally within the interior space 118 of the applicator body 110, and into the piercing element 130. As discussed above, the fluid container 150 is constrained (in this embodiment, by the hexagonal outer surface of the fluid container 150) to allow the rotation of the projection 150 or slot 132 in relation to the other to drive the fluid container 150 linearly in the desired direction. Another embodiment may feature an additional component that would drive the projections 150 along the slots 132 without needing to constrain the rotation of the containment vessel.

In other embodiment, the helical slots 132 are provided on the fluid container and the projections 160 are on the distal cap 130. Other embodiments may utilize complimentary threads on the distal cap 130 and fluid container 150. In further embodiments, the piercing element may move while the fluid container is constrained. According to an exemplary embodiment, the distal cap 130 further includes a plurality of flanges 134 configured to engage with one or more corresponding features at the distal end 114 of the applicator body 110 such that the applicator body 110 and distal cap 130 are engaged in a snap-fit arrangement. In order to facilitate the twisting activation, the applicator body 110 and distal cap are engaged and secured longitudinally but are not locked rotationally, such that the distal cap can rotate relative to the applicator body 110. Other connection mechanisms may also be used to connect the applicator body 110 and distal cap 130.

The twisting mechanism and activation provided herein prevents unintentional activation. This mechanism is less susceptible to unintentional activation during transportation or use. The twisting motion does not happen accidentally during transportation or use.

Figures 8, 9:
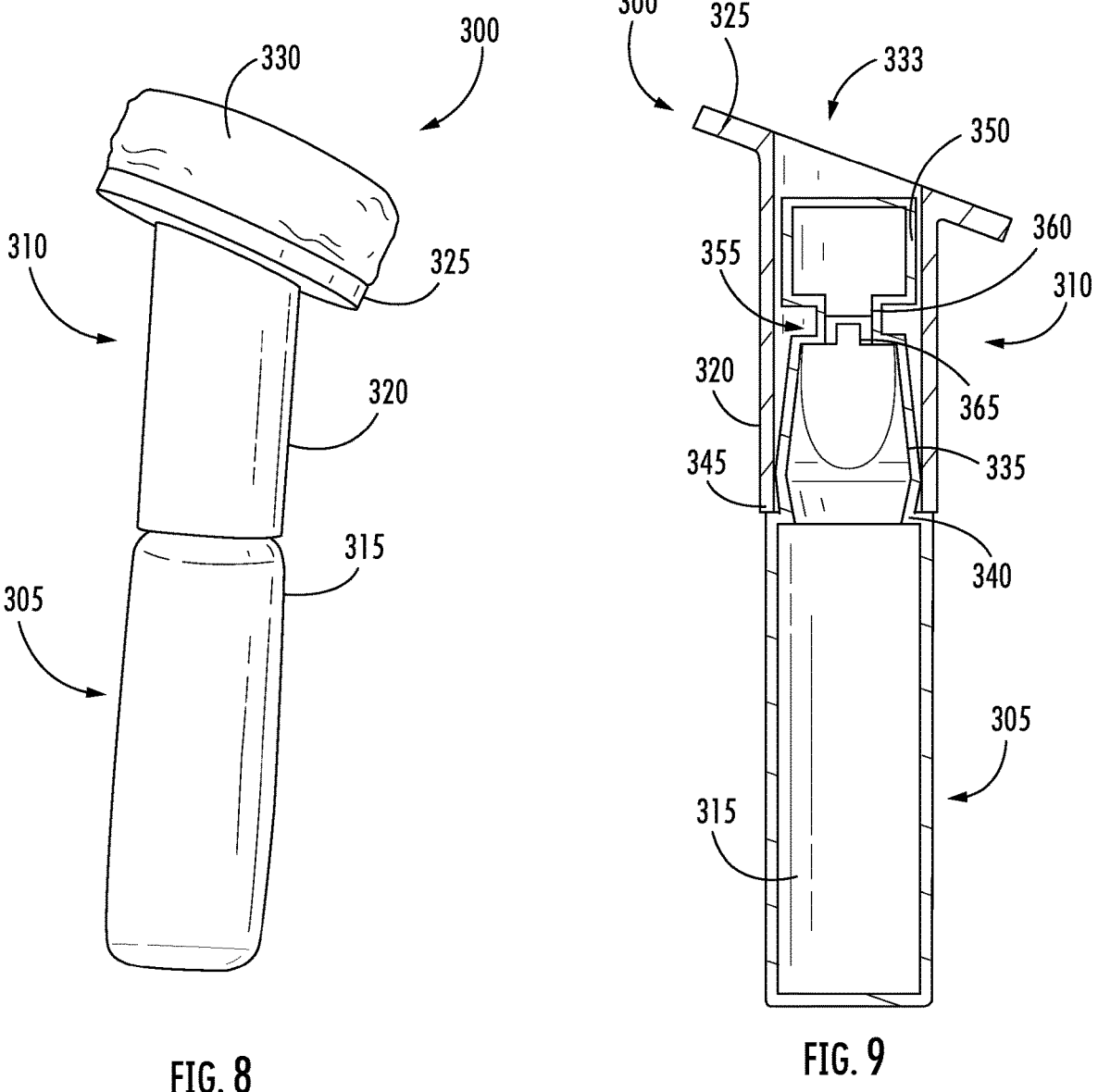
FIG. 8 is a side view of an applicator device, according to an exemplary embodiment.
FIG. 9 is a side cross-sectional view of the applicator device of FIG. 8.

FIG. 8 shows a side view of an applicator device 300, according to another exemplary embodiment. In various implementations, the applicator device 300 may be configured for storing and dispensing one or more solutions for preoperatively preparing a patient's skin or other anatomy. As shown, the applicator device 300 includes a reservoir portion 305, which is coupled to a base portion 310. The reservoir portion 305 is configured to contain one or more solutions (e.g., disinfectants, antibacterial solutions, antiseptics, antimicrobial solutions, antifungal solutions) including, but not limited to, chlorohexidine gluconate. The reservoir portion 305 may include a containment region 315, within which the one or more solutions are contained until application (i.e., onto the patient's skin). As shown in FIG. 8, the containment region 315 is disposed adjacent a generally cylindrical receiving portion 320 of the base portion 310 when the base portion 310 is coupled to the reservoir portion 305.

The base portion 310 includes a support 325, which is disposed at an end of the receiving portion 320 furthest from the containment region 315. The support 325 may have a width that is greater than a width of the receiving portion 320. In various embodiments, the support 325 may be generally circular in shape. In other embodiments, the support 325 may be generally rectangular in shape. As shown, the support 325 may be disposed at an angle relative to a longitudinal axis of the receiving portion 320, for example at an angle between 20 degrees and 45 degrees relative to a longitudinal axis of the receiving portion 320. In other embodiments, the support 325 may be disposed such that a plane defined by the support 325 is substantially perpendicular to the longitudinal axis of the receiving portion 320. The support 325 may be disposed adjacent to an absorbent element 330, which may be permanently or removably coupled to the support 325. In various embodiments, the absorbent element 330 may be a foam or sponge. Accordingly, when the applicator device 300 is used, the absorbent element 330 may receive the at least one solution from the reservoir portion 305, which is held within the base portion 310, and the support 325 may structurally support the absorbent element 330 to facilitate application and distribution of the at least one solution.

As shown in FIG. 9, the receiving portion 320 of the base 310 is configured to removably couple to a top region 335 of the reservoir portion 305, where the base 310 may facilitate distribution and application of the one or more solutions to surface, such as a patient's skin. The top region 335, may be contoured so as to concentrically fit within an inner bore 333 of the receiving portion 320. The receiving portion 320 may be retained on the top region 335 via one or more retention features 345, which are disposed on an interior surface of the receiving portion and are configured to engage with one or more detents (e.g., apertures, recesses, etc.) 340 of the top region 335 to form a friction fit and/or interference fit. In various embodiments, the one or more retention components 345 may include one or more ridges, protrusions, barbs, lips, etc. Although FIG. 9 depicts the one or more retention features 345 disposed at a terminal end of the receiving portion 320, in various embodiments, the one or more retention features 345 may be disposed anywhere along the interior of the receiving portion 320.

The top region 335 includes a tab 350, which is coupled to a tip portion 365. The tip portion 365 and the tab 350 are separable at a joint 355, which includes a frangible seal 360. Accordingly, when the tab 350 is twisted (or otherwise bent, torn, or detached), the seal 360 breaks (or the tab 350 detaches from the tip portion 365), which allows the at least one solution from the containment region 315 to exit through the tip portion 365 and flow to the absorbent element 330, to allow the at least one solution to be applied and/or distributed to a surface on the patient.

Figure 10:
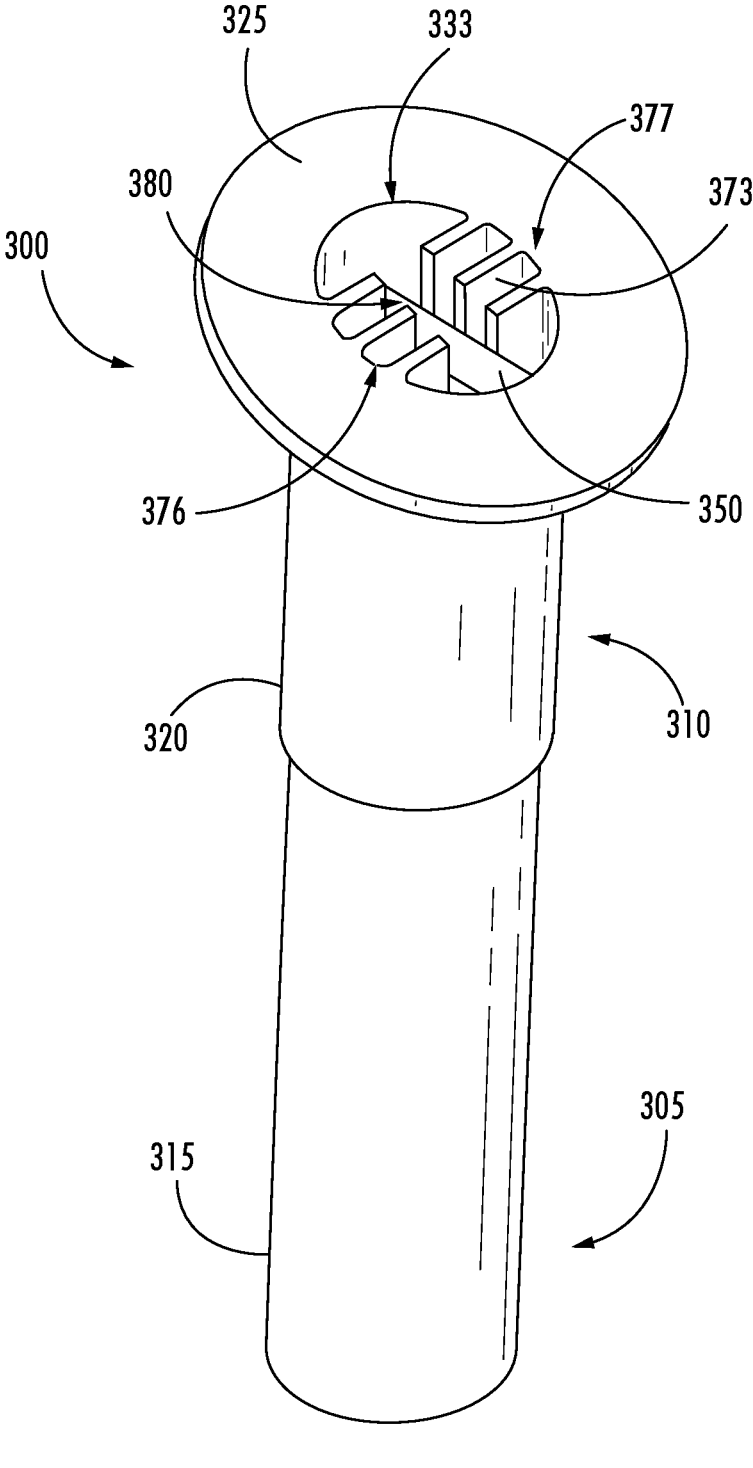
FIG. 10 is a top perspective view of the applicator device of FIG. 8.

As shown in FIG. 10, the support 325 includes a plurality of protruding features 373, which are disposed within the inner bore 333 and arranged adjacent an end thereof. The protruding features 373 extend from a surface of the inner bore 333 toward a central axis of the inner bore 333. In various embodiments, the protruding features 373 are structured to include a first set of features 376 on a first side of the inner bore 333 and a second set of features 377 on a second side of the inner bore 333, where the second set 377 is substantially disposed on an opposite side of the inner bore 333 as the first set 376. In various embodiments, the protruding features 373 are configured to facilitate distribution of the at least one solution received from the reservoir portion 305 to the absorbent element 330. In various embodiments, each of the protruding features 373 is configured as a rectangular rib (i.e., having a rectangular cross-section), where each of the protruding features 373 are spaced a distance from each other. As shown in FIG. 10, the protruding features 373 are positioned such that each of the features 373 is separated and arranged in a substantially parallel arrangement within each of the first set 376 and second set of features 377. As shown in FIG. 10, each of the features 373 within each of the first set 376 and second set 377 are substantially equal in length, and where the first set 376 is spaced from the second set 377 to form a substantially rectangular gap or slot 380 disposed therebetween. In some embodiments, outermost sides (i.e., defined in a direction perpendicular to the slot 380) of each of the first set 376 and the second set 377 are spaced from walls of the receiving portion 320. In other embodiments, each of the first set 376 and the second set 377 are not spaced from walls of the receiving portion 320 (i.e., except for the slot 380).

Figures 11, 12:
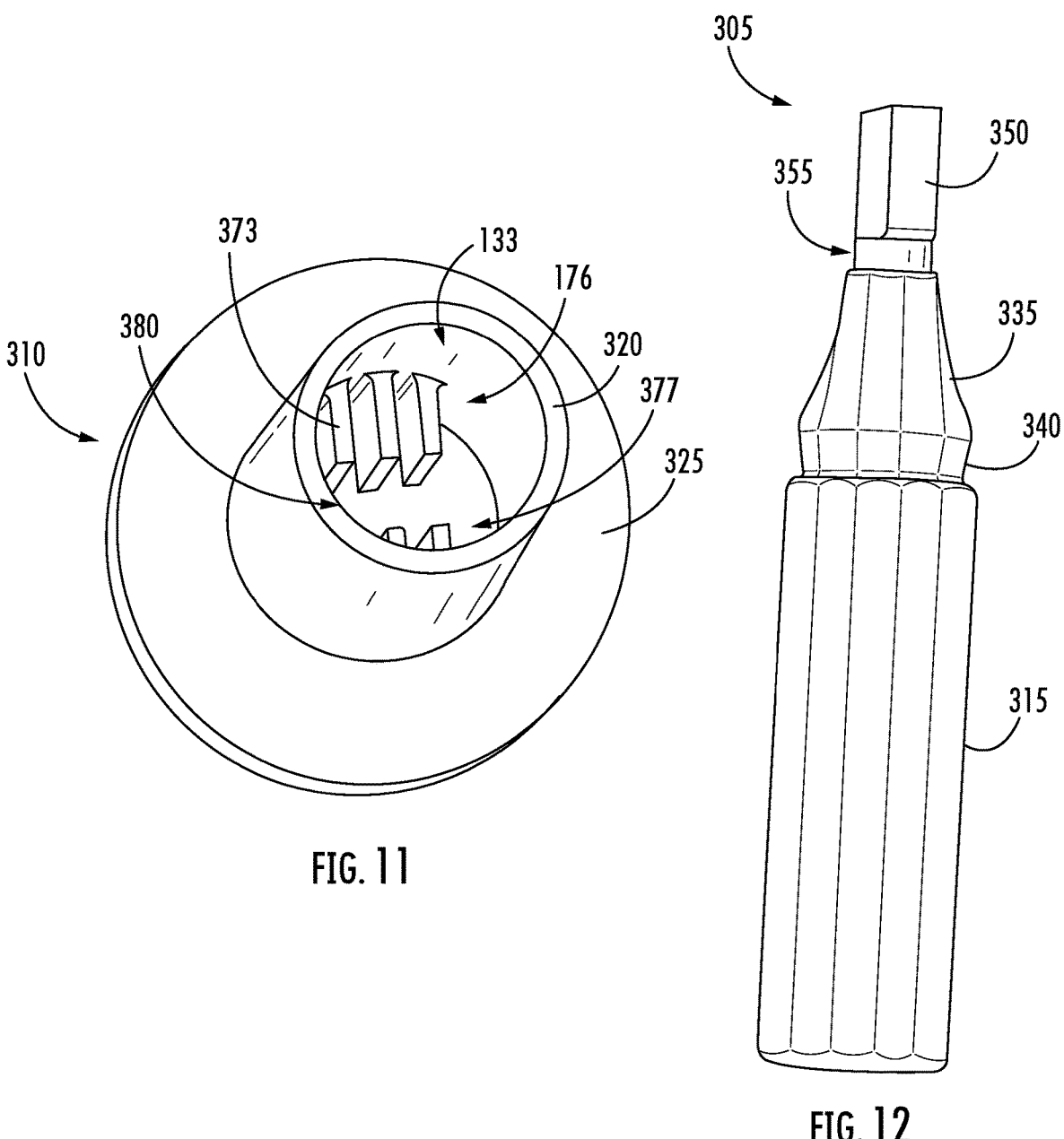
FIG. 11 is a bottom perspective view of a base portion of the applicator device of FIG. 8.
FIG. 12 is a side view of a receptacle portion of the applicator device of FIG. 8.

The slot 380, which is also shown in FIG. 11, is configured to have a width corresponding to a width of the tab 350. In various embodiments, the receiving portion 320 is configured to rotate relative to the top region 335. Accordingly, when the base 310 is coupled to the reservoir portion 305, the base 310 may be rotated (i.e., by gripping and rotating at least one of the support 325 or the receiving portion 320) relative to the containment region 315, which may cause the joint 355 and the frangible seal 360 to be broken to allow the at least one solution within the containment region 315 to flow out of the reservoir portion 305, through the tip portion 365, and the to the absorbent element 330 to be applied and distributed on a surface of the patient.

In various embodiments, the top region 335 may be tapered, as shown in FIG. 12, such that a width or diameter of the top region 335 may decrease from the containment region 315 to the joint 355. In various embodiments, the inner bore 333 of the receiving portion 320 may have a complementary shape to the top region 335 such that an amount of overlap of the receiving portion 320 with the reservoir portion 305 is limited based on an interference with the top region 335 within the inner bore 333. In various embodiments, the top region 335 and the inner bore 333 may be threaded such that rotation of the base relative to reservoir portion 305 may be facilitated by engagement of the threads.

During use of the applicator device 300 (e.g., by medical personnel), the reservoir portion 305 containing at least one solution (e.g., chlorohexidine gluconate (CHG)) may be coupled to the base 310 by sliding the receiving portion 320 over the top region 335 until the one or more retention features 345 engage with the one or more detents 340 and until the tab 350 is received within the slot 380. The base 310 may then be rotated relative to the reservoir portion 305, which may cause the joint 355 and the frangible seal 360 to break. The at least one solution from within the containment region 315 of the reservoir portion 305 may flow through the tip portion 335 to the one or more protruding features 373, which may then facilitate distribution of the at least one solution onto the absorbent element 330. Solution received by the absorbent element 330 may then be applied and distributed to a surface on a patient (e.g., skin) to prepare the surface for further treatments or operations. The absorbent element 330 may be shaped in a such a way that contributes to even distribution of the solution to the surface of the patient. The absorbent element 330 may have a round shape, rectangular shape, trapezoidal shape, or any other shape that would allow for distribution of the solution to difficult to reach areas and/or smaller areas of the surface of the patient (e.g., between fingers or toes, etc.). In various embodiments, the support 325 may have a shape that is complementary to the shape of the absorbent element 330.

In various embodiments, at least one of the base 310 or the reservoir portion 305 may include a biocompatible polymer (e.g., polycarbonate, polyethylene, polypropylene, etc.). In various embodiments, the base 310 may include a biocompatible metallic material (e.g., stainless steel). In various embodiments, the reservoir portion 305 may be disposable. In other embodiments, at least one of the base 310 or the reservoir portion 305 may be structured to withstand sanitization methods including, but not limited to, autoclaving. In some embodiments, the frangible seal 360 may be structured as a region of the joint 355 having a substantially thinner (e.g., in diameter, width, etc.) material thickness as compared to adjacent regions (e.g., the tip portion 365) such that the seal 360 may be more readily severed as compared to other portions of the joint 355. In some embodiments, the joint 355 may include one or more notches, which may facilitate breaking the frangible seal 360. In some embodiments, the reservoir portion 305 may be configured such that the containment region 315 includes one or more flexible regions, which may facilitate deformation of the containment region 315 (e.g., by squeezing) to control and/or accelerate flow of the at least one solution out of the containment region 315. In other embodiments, the containment region 315 may be made of a flexible or deformable material, which may be deformed (e.g., squeezed) to control and/or accelerate flow the at least one solution out of the containment region 315.

Figure 13:
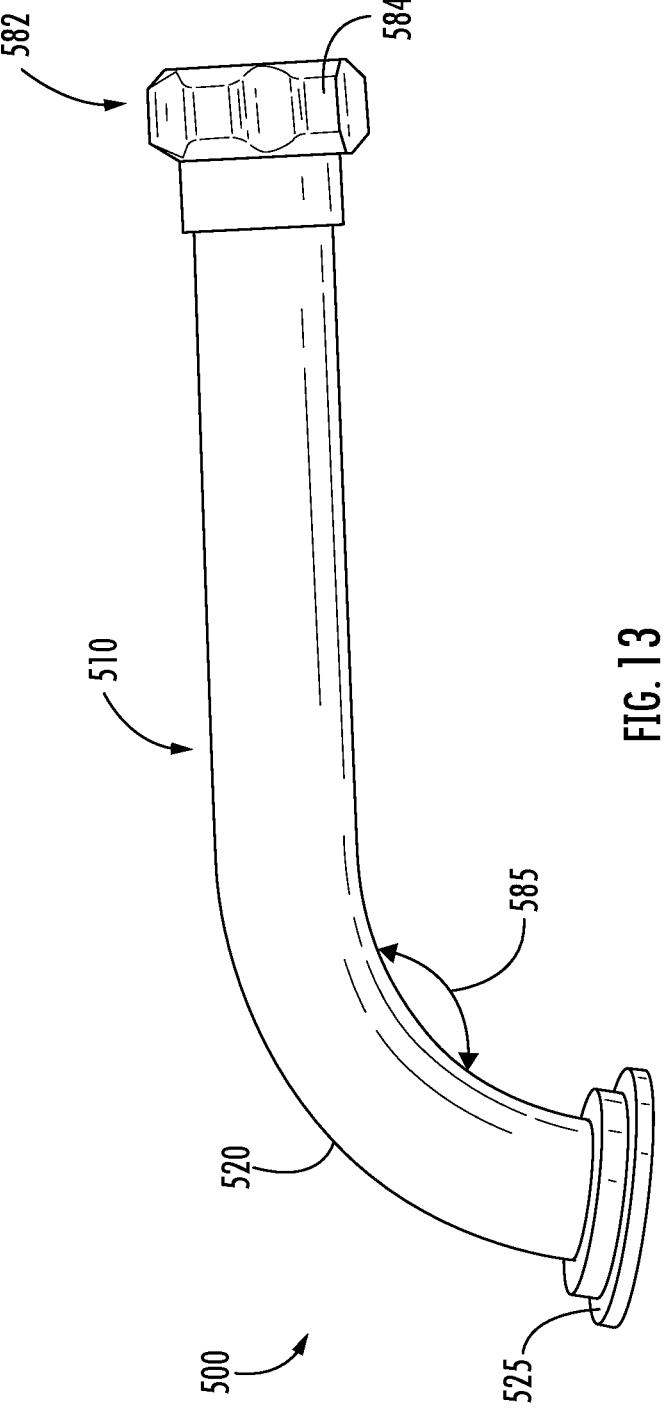
FIG. 13 is a side view of an applicator device, according to an exemplary embodiment.

In some embodiments, an applicator device may be contoured to facilitate ease of use in a variety of use applications, such as the applicator device 500 shown in FIG. 13. In various embodiments, elements 510-580 of the applicator 500 are similar or equivalent to corresponding elements 310-380 of the applicator 300. As shown in FIG. 13, the receiving portion 520 of the base 510 of the applicator 500 may be curved such that an end of the base 510 adjacent the support 525 is curved such that it includes a linear portion and curved portion that is curved away from a primary axis of the linear portion. In some embodiments, the base 510 may be curved such that the support 525 extends away from a primary axis of the applicator device. Curvature of the base 510 may enable ease of handling of the applicator device 500 during application of one or more solutions (e.g., pre-operative cleansing solutions) on a patient treatment surface. In various implementations, the base 510 may be configured to have sufficient curvature to enable a user (e.g., medical personnel) to hold the base portion 510 of the applicator device 500 in a substantially horizontal orientation (e.g., parallel to a patient treatment surface), where curvature of the base 510 facilitates flow of solution to an applicator, which may be coupled to the support 525. The solution may be stored in a reservoir (e.g., similar or equivalent to the reservoir portion 305), which may be inserted into the base 510. In various embodiments, an angle of curvature 585 of the base 510 may be based on a particular use application of the applicator device 500. In some embodiments, the angle of curvature 585 may be greater than 90 degrees. In other embodiments, the angle of curvature 585 may be less than 90 degrees, such as between 20 and 45 degrees.

As shown, an end of the base 510 opposite the end of the base 510 adjacent the support 525 may be coupled to an end cap 582. The end cap 582 may be configured to retain a reservoir of solution within the base 510 during use of the applicator device. In various embodiments, the end cap 582 may be configured to couple to the base 510 via one or more threads. In other embodiments, the end cap 582 may be configured to couple to the base 510 via a friction fit or an interference fit. As shown, the end cap 582 may include one or more ridges or protruding features 584 extending in a radial direction and disposed about a circumference of the end cap 582, where the ridges 584 are structured to facilitate ease of handling of the end cap 582.

Figures 14, 15, 16:
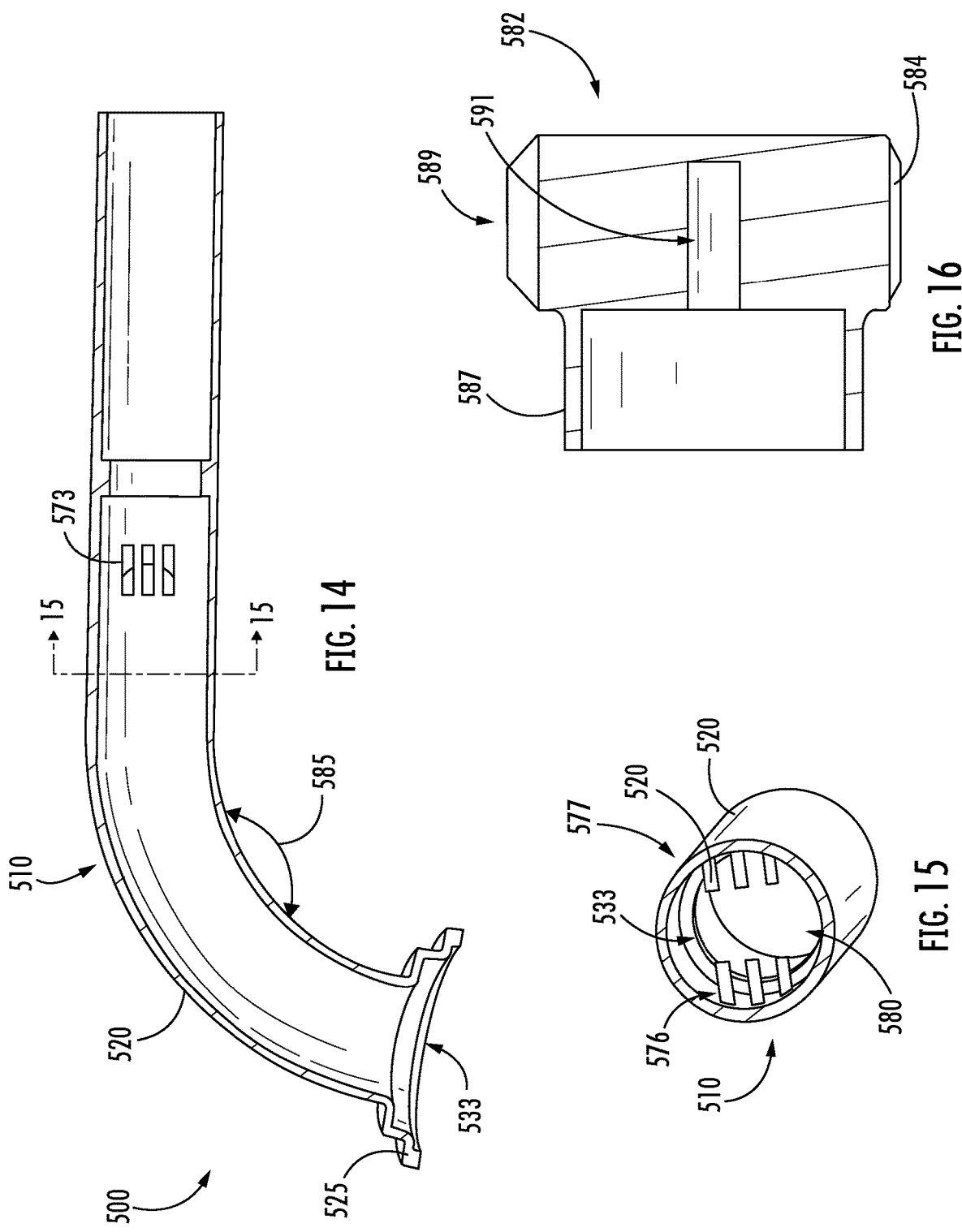
FIG. 14 is a side cross-sectional view of the applicator device of FIG. 13.
FIG. 15 is an end-cross-sectional view of the applicator device of FIG. 13, taken along line 15-15 of FIG. 14.
FIG. 16 is a side cross-sectional view of an endcap of the applicator device of FIG. 13.

As shown in FIG. 14, which is a side cross-sectional view of the applicator device 500, the inner bore 533 of the base 510 includes a plurality of protruding features 573 spaced from the support 525. As shown in FIGS. 14 and 15 (which illustrates a cross-sectional view of the device 500 along line 15-15), the features 573 extend from a surface of the inner bore 533 toward a central axis of the inner bore 533. In various embodiments, the protruding features 573 are structured to include a first set of features 576 on a first side of the inner bore 533 and a second set of features 577 on a second side of the inner bore 533, where the second set 577 is substantially disposed on an opposite side of the inner bore 533 as the first set 576. In various embodiments, the protruding features 573 are configured to facilitate distribution of the at least one solution received from a reservoir disposed within the base 510 to the end of the base 510 adjacent the support 525 (which may be coupled to an absorbent element). In various embodiments, each of the protruding features 573 is configured as a rectangular rib (i.e., having a rectangular cross-section), where each of the protruding features 573 are spaced a distance from each other. As shown in FIG. 15, the protruding features 573 are positioned such that each of the features 573 is separated and arranged in a substantially parallel arrangement within each of the first set 576 and second set of features 577. As shown in FIG. 15, each of the features 573 within each of the first set 576 and second set 577 are substantially equal in length, and where the first set 576 is spaced from the second set 577 to form a substantially rectangular gap or slot 580 disposed therebetween. In some embodiments, outermost sides (i.e., defined in a direction perpendicular to the slot 580) of each of the first set 576 and the second set 577 are spaced from walls of the receiving portion 520. In other embodiments, each of the first set 576 and the second set 577 are not spaced from walls of the receiving portion 520 (i.e., except for the slot 580).

The slot 580 may be configured to have a width corresponding to a width of a reservoir (or a portion thereof) disposed within the base 510. In various embodiments, the receiving portion 520 is configured to rotate relative to a reservoir inserted within the base 510 such that upon rotation of the base 510 or the reservoir, a frangible seal of the reservoir may break to allow solution within the reservoir to flow through the base 510 to be distributed on a surface of the patient. In various embodiments, the end cap 582 may include a first portion 587 and a second portion 589, where the second portion 589 has a larger diameter than the first portion 587 and where the second portion 589 includes the ridges 584. In various embodiments, such as shown in FIG. 16, the second portion 589 of the end cap 582 may include a slot 591, where the slot 591 is configured to receive a portion of a reservoir disposed within the base 510. Accordingly, during use of the applicator device 500, a reservoir having a first locating feature (e.g., a tab similar or equivalent to the tab 350) at a first end and a second locating feature (e.g., a tab similar or equivalent to the tab 350) at a second end may be inserted into the receiving portion 520 of the base 510, where the first locating feature of the reservoir may be inserted into the slot 580. The end cap 582 may be coupled to the end of the base 510 such that the first portion 587 slides over an outer surface of the receiving portion 520 and the second locating feature of the reservoir is inserted into the slot 591 of the second portion 589. The ridges 584 may then be used to twist the end cap 582 relative to the receiving portion 520 of the base 510, which may then break a frangible seal (e.g., a frangible seal similar or equivalent to the seal 360) within the reservoir to allow the at least one solution to flow toward the support and an absorbent element (e.g., similar or equivalent to the absorbent element 330).

Notwithstanding the embodiments described above in FIGS. 1-16, various modifications and inclusions to those embodiments are contemplated and considered within the scope of the present disclosure.

As utilized herein with respect to numerical ranges, the terms "approximately," "about," "substantially," and similar terms generally mean +/-10% of the disclosed values, unless specified otherwise. As utilized herein with respect to structural features (e.g., to describe shape, size, orientation, direction, relative position, etc.), the terms "approximately," "about," "substantially," and similar terms are meant to cover minor variations in structure that may result from, for example, the manufacturing or assembly process and are intended to have a broad meaning in harmony with the common and accepted usage by those of ordinary skill in the art to which the subject matter of this disclosure pertains. Accordingly, these terms should be interpreted as indicating that insubstantial or inconsequential modifications or alterations of the subject matter described and claimed are considered to be within the scope of the disclosure as recited in the appended claims.

It should be noted that the term "exemplary" and variations thereof, as used herein to describe various embodiments, are intended to indicate that such embodiments are possible examples, representations, or illustrations of possible embodiments (and such terms are not intended to connote that such embodiments are necessarily extraordinary or superlative examples).

The term "coupled" and variations thereof, as used herein, means the joining of two members directly or indirectly to one another. Such joining may be stationary (e.g., permanent or fixed) or moveable (e.g., removable or releasable). Such joining may be achieved with the two members coupled directly to each other, with the two members coupled to each other using a separate intervening member and any additional intermediate members coupled with one another, or with the two members coupled to each other using an intervening member that is integrally formed as a single unitary body with one of the two members. If "coupled" or variations thereof are modified by an additional term (e.g., directly coupled), the generic definition of "coupled" provided above is modified by the plain language meaning of the additional term (e.g., "directly coupled" means the joining of two members without any separate intervening member), resulting in a narrower definition than the generic definition of "coupled" provided above. Such coupling may be mechanical, electrical, or fluidic.

References herein to the positions of elements (e.g., "top," "bottom," "above," "below") are merely used to describe the orientation of various elements in the FIGURES. It should be noted that the orientation of various elements may differ according to other exemplary embodiments, and that such variations are intended to be encompassed by the present disclosure.

It is important to note that any element disclosed in one embodiment may be incorporated or utilized with any other embodiment disclosed herein. Although only one example of an element from one embodiment that can be incorporated or utilized in another embodiment has been described above, it should be appreciated that other elements of the various embodiments may be incorporated or utilized with any of the other embodiments disclosed herein.

What is claimed is:

1. An applicator device configured for delivery of at least one solution to a surface, the applicator device comprising:

an applicator body having a head portion comprising an opening, a distal end opposite the head portion, and an outer wall forming an interior space;

a fluid container moveably positioned in the interior space of the applicator body, the fluid container comprising an interior portion for holding the at least one solution and a membrane for preventing passage of the at least one solution out of the interior portion;

a piercing element positioned in the interior space, the piercing element configured to breach the membrane to allow for passage of the at least one solution out of the interior space of the fluid container; and a distal cap coupled to the distal end of the applicator body, the distal cap configured to rotate relative to the applicator body to cause movement of the fluid container relative to the distal cap, such that rotation of the distal cap causes longitudinal movement of the fluid container within the interior space of the applicator body into contact with the piercing element, such that the piercing element breaches the membrane and allows the at least one solution to flow from the fluid container, past the piercing element, and through the opening in the head portion of the applicator body.

2. The applicator device of claim 1, further comprising an absorbent element coupled to the head portion of the applicator body.

3. The applicator device of claim 1, wherein the fluid container further comprises at least one projection extending radially from the fluid container, the at least one projection configured to be received by at least one helical slot in the distal cap, such that rotation of the distal cap causes the at least one projection to move along the at least one helical slot and move the fluid container longitudinally in the interior space of the applicator body into contact with the piercing element.

4. The applicator device of claim 3, wherein the fluid container comprises two projections and the distal cap comprises two helical slots.

5. The applicator device of claim 1, wherein the fluid container further comprises a helical slot configured to receive at least one projection extending from the distal cap, such that rotation of the distal cap causes the at least one projection to move along the helical slot and move the fluid container longitudinally in the interior space of the applicator body into contact with the piercing element.

6. The applicator device of claim 1, wherein the applicator body further includes one or more gripping elements to aide in gripping the applicator device by a user.

7. The applicator device of claim 1, wherein the membrane is formed of a plastic, a foil, or other frangible material.

8. The applicator device of claim 1, wherein an exterior surface of the fluid container comprises a hexagonal cross-section.

9. The applicator device of claim 1, wherein the interior space of the applicator body comprises at least one area having a decreased diameter, configured to interact with the fluid container to prevent rotation of the fluid container within the interior space.

10. The applicator device of claim 9, wherein the at least one area having a decreased diameter forms a hexagonal bore in the interior space to interact with a hexagonal exterior surface of the fluid container.

11. The applicator device of claim 1, wherein the head portion comprises a connection end formed in a triangle shape.

12. The applicator device of claim 11, wherein the triangle shape of the connection end is complementary to a shape of an absorbent element attached thereto.

13. The applicator device of claim 11, wherein a plane of the connection end is disposed at an angle relative to a longitudinal axis of the applicator body.

14. The applicator device of claim 1, wherein the piercing element comprises a tip and a base portion.

15. The applicator device of claim 1, wherein the piercing element comprises a frame forming a plurality of openings to facilitate a flow of fluid therethrough.

16. A method of dispensing at least one solution for preoperative preparation of a patient's skin, comprising:
   obtaining an applicator device, the applicator device comprising:
      an applicator body having a head portion comprising an opening, a distal end opposite the head portion, and an outer wall forming an interior space;
      a fluid container moveably positioned in the interior space of the applicator body, the fluid container comprising an interior portion for holding the at least one solution and a membrane for preventing passage of the at least one solution out of the interior portion;
      a piercing element positioned in the interior space, the piercing element configured to breach the membrane to allow for passage of the at least one solution out of the interior space of the fluid container; and
      a distal cap coupled to the distal end of the applicator body;
   twisting the distal cap relative to the applicator body thereby causing the distal cap to rotate relative to the applicator body to cause movement of the fluid container relative to the distal cap, such that rotation of the distal cap causes longitudinal movement of the fluid container within the interior space of the applicator body into contact with the piercing element, such that the piercing element breaches the membrane; and
   allowing the at least one solution to flow from the fluid container, past the piercing element, and through the opening in the head portion of the applicator body.

17. The method of claim 16, wherein the fluid container further comprises at least one projection extending radially from the fluid container, the at least one projection configured to be received by at least one helical slot in the distal cap, such that rotation of the distal cap causes the at least one projection to move along the at least one helical slot and move the fluid container longitudinally in the interior space of the applicator body into contact with the piercing element.

18. The method of claim 16, wherein the fluid container further comprises a helical slot configured to receive at least one projection extending from the distal cap, such that rotation of the distal cap causes the at least one projection to move along the helical slot and move the fluid container longitudinally in the interior space of the applicator body into contact with the piercing element.

19. The method of claim 16, wherein the piercing element comprises a frame forming a plurality of openings to facilitate a flow of fluid therethrough.

20. The method of claim 16, wherein the applicator device further comprises an absorbent element coupled to the head portion of the applicator body, and wherein the method further comprising applying the at least one solution to the patient's skin using the absorbent element.

* * * * *